United States Patent [19]

Fraenkel

[11] 4,426,719

[45] Jan. 17, 1984

[54] PRODUCTION OF MONOCHROMATIC X-RAY IMAGES OF X-RAY SOURCES AND SPACE RESOLVING X-RAY SPECTRA

[75] Inventor: Benjamin S. Fraenkel, Jerusalem, Israel

[73] Assignee: Yissum Research Development Co. of the Hebrew University of Jerusalem, Jerusalem, Israel

[21] Appl. No.: 234,510

[22] Filed: Feb. 12, 1981

[51] Int. Cl.³ .............................................. G01B 15/00
[52] U.S. Cl. ......................................... 378/70; 378/84
[58] Field of Search ........................ 378/84, 85, 71, 70

[56] References Cited

U.S. PATENT DOCUMENTS 2,474,240  6/1949  Friedman ............................. 378/84
3,927,319 12/1975  Wittry ................................... 378/85

OTHER PUBLICATIONS

Johansson, T., "Ueber ein neuartiges, genau tokussierendes Roentgenspektrometer" *Z. Physik*, 82, 507–528, (1933).
Renninger, M. "'Umweganregung', eine bisher unbeachtete Wechselwirkungserscheinung bei Raumgitterinterferenzen" *Z. Physik*, 106, 141–176, (1937).
Fraenkel, B. S., "(2,2,2) Reflections of GE, SI and Diamond Taken on a Double Reflection Camera for X-Ray Crystallography", *Bull. Res. Counc. Israel*, 6A 125–130 (1957).
Fraenkel, B. S. "Double Reflection X-Ray Camera", Rev. Sc. Instruments, 29, 726–727 (1958).
Fraenkel, B. S., "Monochromatic X-Ray Images of X-Ray Emitting Sources", *Appl. Phys. Lett.*, 36, 4, pp. 341–343, 2-15-80.
Fraenkel, B. S., "Space Resolved *X-Ray Spectroscopy for Tokomak*" *X-Ray Spectrometry*, vol. 9, No. 4, pp. 189–194 (1980).

*Primary Examiner*—Alfred E. Smith
*Assistant Examiner*—T. N. Grigsby
*Attorney, Agent, or Firm*—Browdy and Neimark

[57] ABSTRACT

The present method and apparatus produces undistorted x-ray images of sources emitting x-rays and especially of certain areas emitting x-rays. Stigmatic monochromatic x-ray images, and x-ray spectra with a spatial resolution along the lines of the spectrum are produced. The device comprises, in combination, an x-ray diffraction crystal capable of simultaneous reflection, and an x-ray point intensity measuring system, the arrangement being such that the reflection plane of the crystal makes an angle with the plane of the intensity measurement system of 90 degrees of angle minus the Bragg angle for a forbidden reflection of the crystal, and where the x-ray radiation incident on the crystal makes a Bragg angle with the plane of the forbidden reflection, the azimuthal arrangement allowing simultaneous reflection. A source of x-rays forms, by means of double reflection from a plane crystal of adequate size, a plurality of undistorted spectral images, each of which corresponds to a given wavelength of the x-ray emitter. When x-rays from a suitable source are incident on a crystal of suitable curvature, and by double reflection, a spectrum is obtained, each line corresponding to a given wavelength, the variation of density along each line being indicative of the spatial distribution of the emitter of each line in the direction of such line.

11 Claims, 7 Drawing Figures

PRODUCTION OF MONOCHROMATIC X-RAY IMAGES OF X-RAY SOURCES AND SPACE RESOLVING X-RAY SPECTRA

FIELD OF THE INVENTION

The present invention relates to a method and apparatus for producing undistorted images of x-ray sources. The present invention also relates to a method and apparatus for producing spectral images of x-ray sources and especially of certain areas which emit such x-rays, resulting in the formation of a spectrum wherein each wavelength of x-rays emitted forms a sharp line, the variations of intensity along such lines being indicative of the spatial distribution of density of the emitter of said x-rays in the direction of said lines.

BACKGROUND OF THE INVENTION

High temperature plasmas and various other sources emit x-rays. Spectroscopy provides means for classifying such radiations and makes it possible to determine atoms, ions and level transitions involved. It would be of great value to be able to carry out such determinations with spatial resolution in a simple and convenient manner by comparatively simple means.

Hitherto rather cumbersome and complicated means have been resorted to for x-ray measurements with spatial resolution. Spectroscopy has never been carried out in such manner as to result in both good spatial and energy resolution. Soller slit systems have been used in x-ray and astrophysical spectroscopy. Such systems are complicated, wasteful of energy as much of the radiation is blocked, comparatively expensive and result only in a very limited partial spatial resolution. High resolution curved x-ray spectrometers are described by Johansson in Z. Physik, 82,507 (1933), but these do not provide means for attaining a spatial resolution.

The effect of double reflections, also known as simultaneous reflections, is known in crystollagraphy, as for example from the articles of Renninger, Z. Physik, 106, 141 (1937) and Fraenkel, Bull. Res. Counc. Israel, 6A, 125 (1957) and Rev. Sc. Instr., 29, 726 (1958). The latter references disclose that at least single diamond, germanium and silicon crystals are capable of such double reflections. This effect was described as a scientific curiosity and no use has been hitherto for the applicative nature of this phenomenon.

SUMMARY OF THE INVENTION

The present invention relates to a method of producing undistorted images of x-ray sources. The novel method according to the present invention results in an image of the x-ray source and especially of a given area emitting such x-rays, when a plane crystal capable of double reflection is used, and when a curved crystal capable of double reflection is used, results in a spectrum wherein each wavelength emitted by such source results in a sharp and distinct line, the variation of intensity along such lines being indicative of the spatial distribution of the density of the source in the direction of the lines, and the variation of width of the lines being indicative of the ion temperature spatial distribution.

Furthermore, the present invention relates to means for producing stigmatic monochromatic x-ray images and x-ray spectra with a spatial resolution along the lines of the spectrum, and to means for evaluating such spectra and for determining the various critical parameters of the source of such x-rays.

The invention also relates to the curved crystal itself, capable of double reflectance and usable in the method and device of the present invention.

The novel method and device can be used for measurement of high temperature plasmas and for measurements of other sources of such x-rays. According to the present invention it is possible to classify the radiation and to determine the identity of the atoms, ions, etc., involved and the level transitions of same. It is furthermore possible to obtain a clear picture of the spatial distribution of the source of the x-rays and such picture of high resolution is obtained in a convenient and simple manner by comparatively simple and inexpensive means.

According to the present invention it is possible, for example, to examine plasmas produced by laser radiation and to obtain a spatial resolution of same for each wavelength emitted. It is also possible to obtain the distribution of ions and the ionic temperature about the central ring of a Tokamak or other nuclear fusion device.

One embodiment of the present invention is essentially a curved-crystal spectrometer, the arrangement being such that the crystal is adjusted to reflect incident x-rays through double reflection, resulting in the desired spectrum with spatial and energy resolution along the lines of said spectrum. Another embodiment uses a planar crystal with double reflection, resulting in spectral images.

BRIEF DESCRIPTION OF THE DRAWINGS

The invention and its underlying physical principles are explained and illustrated with reference to the enclosed schematical drawings, which are not according to scale and in which.

DETAILED DESCRIPTION OF PREFERRED EMBODIMENTS

Figure 5:
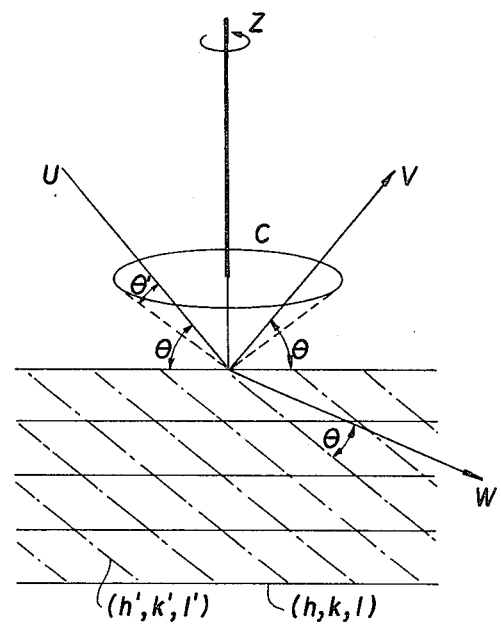
FIG. 5 illustrates double reflection on a crystal.

The method in accordance with the present invention uses the crystallographic reflection property called simultaneous or double reflection. This known phenomenon can be briefly explained with reference to FIG. 5. Assume that a well defined monochromatic x-ray beam U stikes a crystallographic plane with a Bragg angle $\theta$. Let the Bragg reflection involved be a forbidden reflection. No intensity will be reflected because of extinction. However, as one rotates the crystal about an axis Z perpendicular to the plane, one will observe that in some crystals, in special azimuthal positions, for appropriate forbidden reflection planes, the beam will be reflected in the 'forbidden' direction V. This comes about when the incoming beam fulfills the Bragg condition for two planes at once in the specific azimuthal position. It will strike the planes (hkl) with the Bragg angle θ, but will not be reflected because of extinction involved in the forbidden reflection. The same beam will, however, strike also the planes (h'k'l') with the Bragg angle θ'. If this reflection is allowed the beam will be reflected into the direction W. It may be shown that then another family of planes exists which will rereflect the beam W into the forbidden direction V. This will be correct for a given direction of the beam, a given azimuthal position of the crystal relative to the beam, and a given monochromatic wavelength. For a slightly different wavelength and for the same source of the incoming beam, the crystal must be rotated slightly about the axis Z to obtain the same effect. An object emitting a given wavelength will form, through the double reflection process, an image by a beam of parallel radiation reaching the crystal. For another emitted wavelength, a parallel beam at an angle with the first beam will form another such image.

Figure 6:
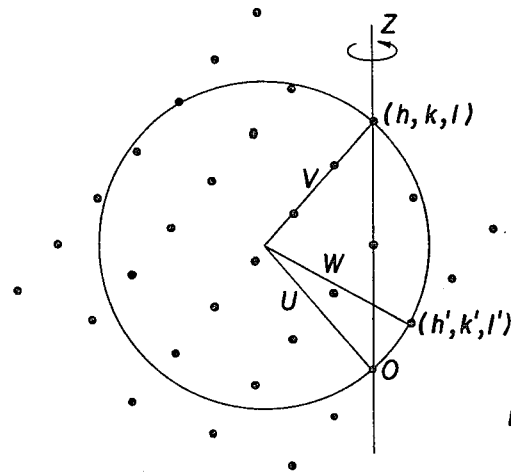
FIG. 6 illustrates the reciprocal lattice and reflecting sphere for the crystal as described in FIG. 5.

In terms of the reciprocal lattice, it would mean that in addition to the point representing the forbidden reflection h, k, l, there is also an additional reciprocal lattice point h', k', l', touching the Ewald sphere. So reflection may be done by the double process through h', k', l'; and h-h', k-k', l-l', as shown in FIG. 6.

The physical basis of the method and of the device of the present invention is as follows:

X-ray radiation emitted from a source of such rays may be reflected according to Bragg's law by a crystallographic plane. The radiation originating from each point of the said source emits a certain x-ray wavelength, and this is reflected not only in one direction, but in many directions, through a Kossel cone, as shown with reference to FIG. 1 where A is a point source of x-rays, 11 is a suitable crystal, and where θ is the Bragg angle. If the reflection is "forbidden", there might exist a direction in which reflection is allowed for a given wavelength, i.e. the direction A-A'-A". This physical phenomenon, which was described by Renninger and also by Fraenkel, is the basic phenomenon which is made use of in the present invention.

Figure 1:
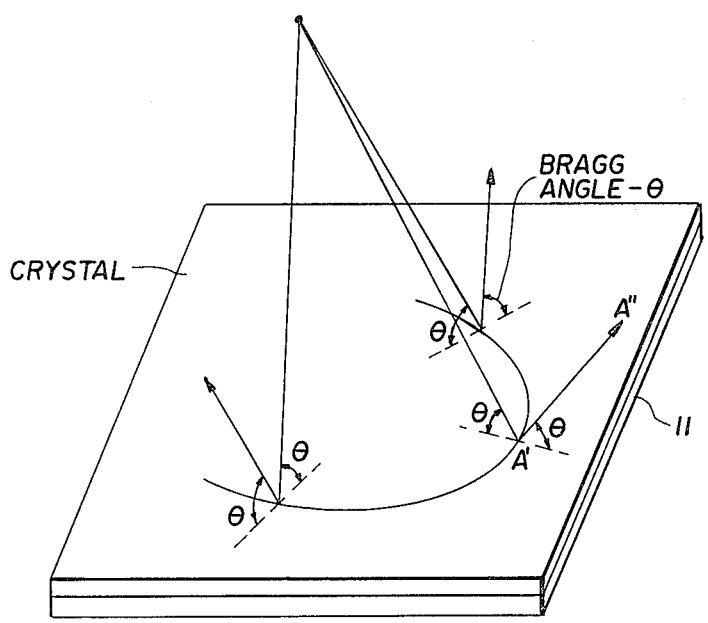
FIG. 1 illustrates reflections of x-rays from a crystal plane.
Figure 2:
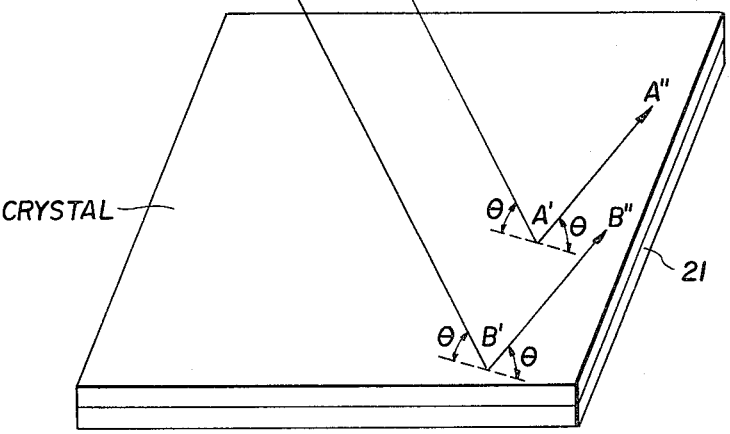
FIG. 2 illustrates the reflection of x-rays from a crystal plane by double reflection.

As shown in FIG. 1, the point source A is reflected monochromatically in the direction A'-A". As shown in FIG. 2, this will also happen with another point source B, which emits the same radiation, and the direction of B'-B" will be parallel to A'-A". The same will be true for other point sources. Thus any point of the emitting source which is situated relative to the crystal 21 so that radiation coming from it parallel to A-A' will reach the crystal, will result in a parallel reflection thereof. Thus, a continuous x-ray emitting surface, constituting a multitude of points, will be reflected in an undistorted way through the double reflection process so as to provide a monochromatic undistorted picture of the source.

Figure 3:
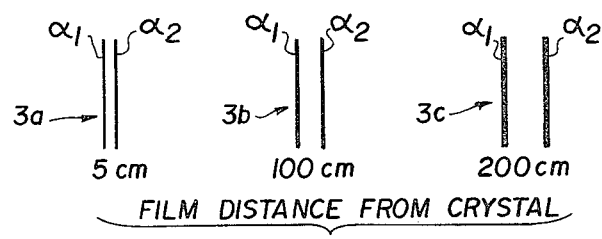
FIG. 3 illustrates image formation of an anticathode at different distances.

Since the radiation participating in the image-forming process is strictly parallel at one fixed wavelength, the dimensions of the image do not vary with distance of the film from the crystal. It is seen from FIG. 3, that though the pictures (images) of the source which have different wavelengths will separate from each other, each such picture (image) of a given monochromatic wavelength maintains its dimensions without distortion as the distance from the crystal grows. In this Figure, 3a illustrates the reflection of the radiation from a line of the anticathode in an x-ray tube with the film at a distance of 5 cm from the crystal; 3b shows such reflection at about 1 m distance and 3c shows such reflection at about 2 m from the crystal. The radiation shown here is that of $CuK_{\alpha 1}$ and $CuK_{\alpha 2}$. It is evident that the length of the line representing the anticathode does not change, whereas the distance between the two lines increases proportionally to the distance of the film from the crystal.

A curved crystal x-ray spectrometer with a crystal of large dimensions reflecting in the plane of the Rowland circle via double reflection will give space resolution along the spectral lines. The Johansson x-ray spectrometer gives highly resolved lines, but without spatial resolution. The novel system illustrated with reference to FIG. 4 is equal in its performance to that of an infinitely dense Soller slit system which allows only radiation parallel to the Rowland circle to pass from the source to the Rowland circle, yet it results in a larger intensity of the image lines which can be obtained, it is simple and elegant and has a much better accuracy.

The method of this embodiment of the present invention comprises directing radiation from an x-ray source onto a bent crystal capable of giving double reflection, such as a single Ge crystal forming part of a Rowland cylinder in the same manner as a conventional curved crystal x-ray spectrometer. This crystal is ground and bent in such manner that the crystal can double reflect approximately in the plane of the Rowland circle, i.e. perpendicular to the axis of this cylinder, for a given x-ray wavelength range. This results in the formation of an image of the source in the form of distinct lines corresponding to the various wavelengths of the emitter on the Rowland cylinder. The intensity of said lines along their length can than be evaluated to determine the corresponding spatial intensity in the source. Furthermore, the variation of the width along the length of the lines can be evaluated to determine the corresponding spatial temperature distribution in the source.

By this system and by this method it is possible to obtain space and time-resolved information from hot plasmas, and also from plasmas of the type produced in devices of the Tokamak type, which is not attainable by conventional techniques.

Figure 4:
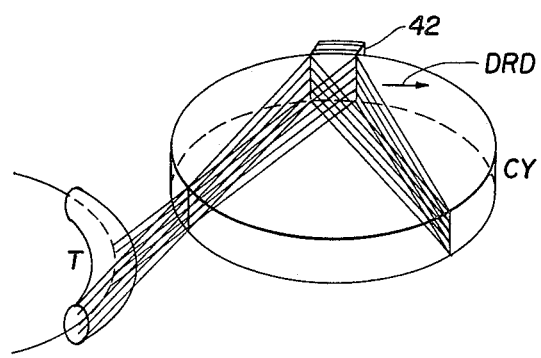
FIG. 4 illustrates a curved crystal spectrometer reflecting via double reflections.

This principle is illustrated with reference to FIG. 4, showing a device in accordance with the present invention, for forming space-resolved x-ray spectra. The device is essentially similar to a Johansson spectrometer, comprising Rowland cylinder CY, wide open for the entrance of radiation coming from an x-ray source T, which radiation is incident on the curved crystal 42, which is chosen and positioned in such manner as to exhibit double reflection approximately in the plane of the Rowland circle. The double reflection direction is indicated by DRD. Accordingly, reflection is only allowed to take place for radiation parallel to the plane of the Rowland circle by means of double reflection. The incident radiation results in the formation of a spectrum, each line of which corresponds to a given wavelength of the x-ray emitter, the variation of intensity along each line being indicative of the spatial distribution of the emitter of said line in the direction of such line. Thus, for each line there is obtained a spatial resolution along the line, indicating the source intensity distribution for each line perpendicular to the Rowland circle. Only rays perpendicular to the axis of the Rowland circle participate in the line forming process. The spectrum can be recorded on a suitable film, or measurements can be effected by means by suitable measurement means.

Figure 7:
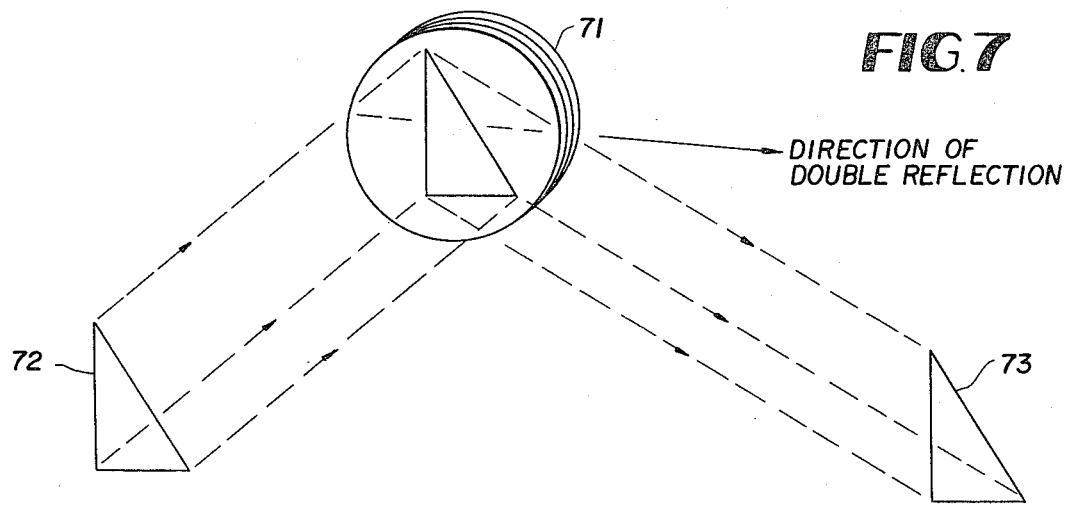
FIG. 7 illustrates imaging of an x-ray emitting surface by a plane crystal by double reflection.

Image formation by means of a plane crystal 71, exhibiting double reflection in the direction indicated is illustrated in FIG. 7. The source 72 forms an image 73. As the crystal is chosen to be of adequate size, a source of x-rays forms by double reflection from such crystal a plurality of spectral images, each of which corresponds to a given wavelength of the emitter. To permit such spectral images it is necessary for the area of the crystal to be substantially larger than the source. Such area will usually be larger than 25 mm$^2$ and for many applications will be on the order of 150–200 mm$^2$ or even larger, perhaps substantially larger. Instead of the film there may be used a plurality of counters, which provide the same result, with time resolution.

Any monochromatic radiation coming from the source, which is not nearly parallel to a given direction specific to that wavelength, will not be reflected by the crystal even if it is incident on the crystal at the above Bragg angle, as it will not be incident at the direction at which the double reflection takes place, and it will become extinct due to the forbidden reflection plane.

In order to assure proper double reflection resolution the apparatus using such a plane crystal should include means for adjusting the relative positions of the crystal and the film or other measurement device so as to achieve the proper Bragg angle for the given crystal and wavelength to be measured and means for azimuthally adjusting the crystal about an axis perpendicular to the reflecting plane in order to allow the desired double reflection.

It is possible to use a device according to the present invention in order to reflect parallel beams of monochromatic radiation of an anticathode, which may be used for medical purposes. This makes possible reproducible x-ray diagnostics with a much improved resolution, which could not be attained hitherto.

With the device according to the present invention it is possible to obtain pictures of solar flares with spatial and energy resolution. It is also possible to obtain space and energy resolved images of intense x-ray sources such as plasma implosions, of experiments simulating atomic explosions and of other processes where x-rays are emitted.

To further the explanation, understanding and disclosure of the present invention, the entire contents of the publications of the present inventor at *Appl. Phys. Lett.*, 36, 4, pp. 341–343, Feb. 15, 1980, and *X-Ray Spectrometry*, 9, 4, 1980, pp. 189–194, are hereby incorporated by reference. Both of these references specifically recite use of a single Ge crystal.

It will be obvious to those skilled in the art that various changes may be made without departing from the scope of the invention and the invention is not to be considered limited to what is shown in the drawings and described in the specification.

What is claimed is:

1. A crystal for use in space-resolving x-ray spectroscopy, comprising:
   a crystal capable of double reflection, curved in the manner of the crystal of a curved crystal x-ray spectrometer, wherein the curvature of said crystal is such that the plane of double reflection is perpendicular to the axis of the cylindrical curvature of the crystal.

2. A crystal in accordance with claim 1 wherein said crystal capable of double reflection is a single germanium crystal.

3. In a curved crystal x-ray spectrometer having, on the Rowland cylinder thereof, a curved crystal and collection means for detecting or recording the spectra reflecting from the crystal, the improvement, whereby there are produced space resolving x-ray spectroscopic lines, wherein the curved crystal is a crystal in accordance with claim 1.

4. A spectrometer according to claim 3, wherein said collection means is a photographic film.

5. A spectrometer according to claim 3, wherein said collection means comprises suitable counters.

6. A spectrometer in accordance with claim 3 wherein said crystal capable of double reflection is a single germanium crystal.

7. A method for obtaining stigmatic monochromatic x-ray image and x-ray spectra, with spatial resolution along the spectral lines, of a source emitting x-rays along an extended spatial profile, comprising:
   arranging an x-ray diffraction crystal capable of double reflection, in such a manner with respect to said x-ray source that the x-rays emitted from said source along at least a substantial portion of the extended spatial profile thereof are directed toward said crystal at an angle equal to a Bragg angle of forbidden reflection;
   arranging a collector with respect to said crystal such as to receive the x-rays reflected from said crystal by double reflection at the same Bragg angle toward which the x-rays are directed to said crystal;
   exposing said crystal to the x-rays emitted from said source; and
   collecting at said collector the x-rays reflected from said crystal during said exposure,
   wherein said source, crystal and collector remain stationary with respect to one another throughout x-ray collection by said collector.

8. A method according to claim 7, wherein said x-ray diffraction crystal capable of double reflection is a curved diffraction crystal arranged on the Rowland cylinder of a curved crystal x-ray spectrometer, and wherein the curvature of said crystal is such that said curved crystal is capable of double reflection approximately in the plane of the Rowland circle for a given x-ray wavelength range when in use, whereby the reflected spectral lines are formed on the Rowland cylinder with spatial resolution.

9. A method according to claim 7, wherein the crystal capable of simultaneous reflection is planar, whereby each wavelength incident on the crystal is reflected in such manner so as to define a separate stigmatic monochromatic image of the surface emitting the x-rays.

10. A method according to claims 7, 8 or 9 wherein said crystal capable of double reflection is a single diamond, germanium or silicon crystal.

11. A method in accordance with claim 7, 8 or 9, wherein the source emitting x-rays is a polychromatic source.

* * * * *